United States Patent
Bae

(10) Patent No.: US 8,337,439 B2
(45) Date of Patent: Dec. 25, 2012

(54) SPLINT FOR ORTHOPEDICS AND METHOD OF MANUFACTURING THE SAME

(76) Inventor: Jin-Woo Bae, Yongin (KR)

( * ) Notice: Subject to any disclaimer, the term of this patent is extended or adjusted under 35 U.S.C. 154(b) by 672 days.

(21) Appl. No.: 12/441,898

(22) PCT Filed: Mar. 2, 2007

(86) PCT No.: PCT/KR2007/001043
§ 371 (c)(1),
(2), (4) Date: Nov. 11, 2009

(87) PCT Pub. No.: WO2008/035837
PCT Pub. Date: Mar. 27, 2008

(65) Prior Publication Data
US 2010/0063431 A1    Mar. 11, 2010

(30) Foreign Application Priority Data
Sep. 18, 2006  (KR) .................. 20-2006-0089975

(51) Int. Cl.
*A61F 5/00* (2006.01)
(52) U.S. Cl. ..................... 602/8; 602/5; 602/6
(58) Field of Classification Search ............. 602/5–8, 602/60; 206/440–441
See application file for complete search history.

(56) References Cited

U.S. PATENT DOCUMENTS

| 5,171,208 | A | 12/1992 | Edenbaum et al. |
| 5,318,504 | A | 6/1994 | Edenbaum et al. |
| 5,520,621 | A | 5/1996 | Edenbaum et al. |
| 7,172,565 | B2 * | 2/2007 | Termanini .......... 602/8 |

* cited by examiner

Primary Examiner — Kim M Lewis
(74) Attorney, Agent, or Firm — Christopher Paul Mitchell

(57) ABSTRACT

A splint for orthopedics for supporting the affected part of a patient suffering from a fracture or a sprain. A splint includes a support having 500~1500 g/m² of polyester non-woven fabric coated with a water-curable resin, an aluminum casing having a combination of polyethylene, aluminum and nylon (or polyester) in a pouch form to completely prevent the permeation of water so as to prevent the affected part from festering due to water, and a skin-protecting layer having polypropylene non-woven fabric and an outer surface layer having 200~400 g/m² of polyester, polypropylene or nylon, which are sequentially formed on the support. Unlike conventional splints for orthopedics which include a skin contact layer, a surface layer, and a support therebetween, the splint of the invention has a structure in which the support is directly packed with an aluminum casing, and an outer surface layer and a skin-protecting layer are provided thereon.

2 Claims, 2 Drawing Sheets

[Fig. 1]
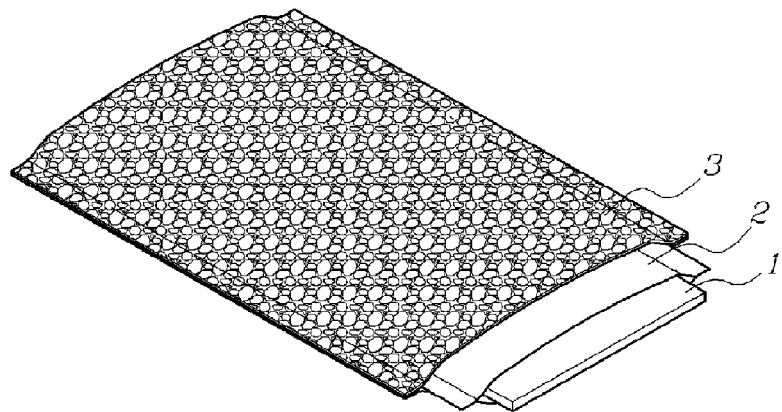
[Fig. 2]
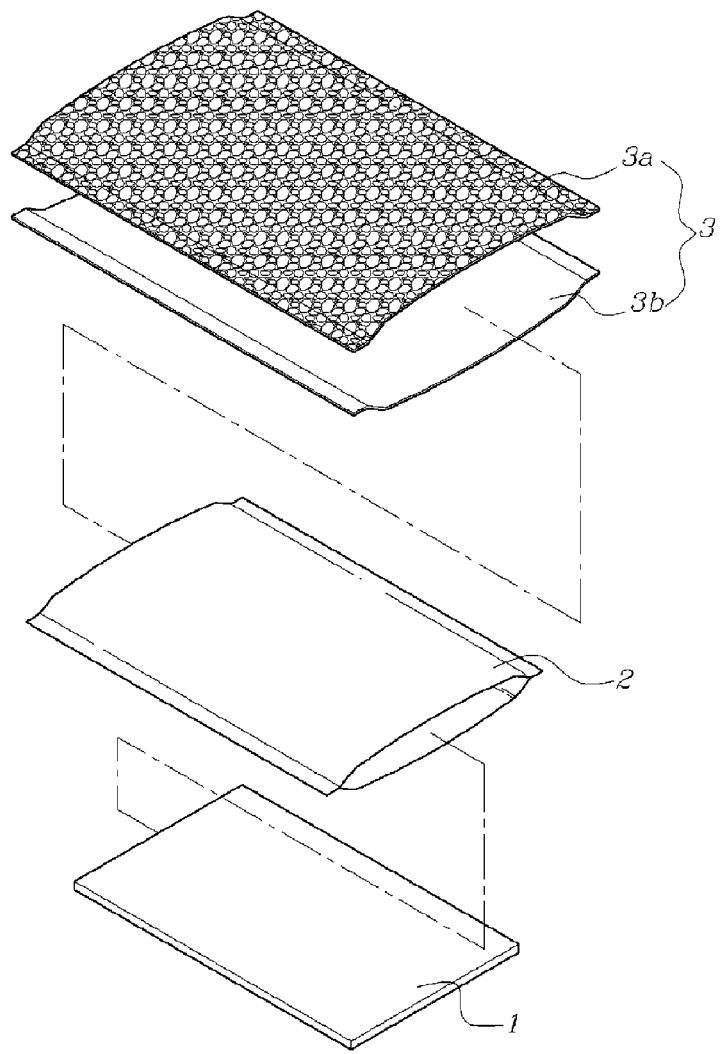

[Fig. 3]
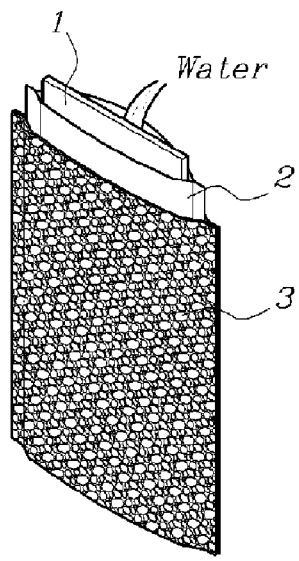
(a)
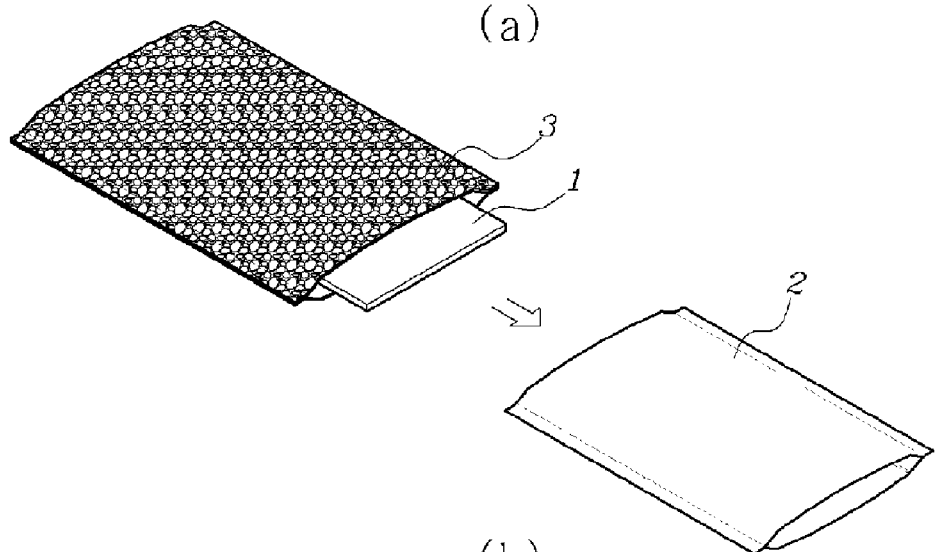
(b)
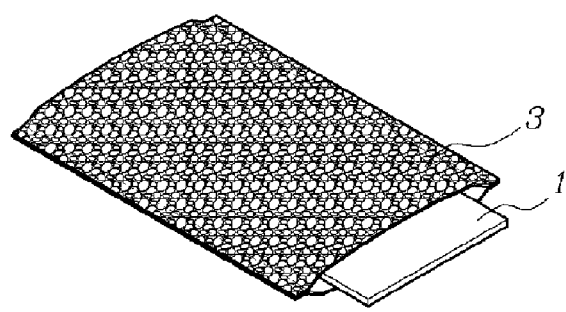
(c)

SPLINT FOR ORTHOPEDICS AND METHOD OF MANUFACTURING THE SAME

RELATED APPLICATIONS

This application is a 371 application of International Application No. PCT/KR2007/001043, filed Mar. 2, 2007, which in turn claims priority from Korean Patent Application No. 10-2006-0089975, filed Sep. 18, 2006, both of which are incorporated herein by reference.

TECHNICAL FIELD

The present invention relates, generally, to a splint for orthopedics for supporting an affected part of a patient suffering from a fracture or a sprain, and, more particularly, to a splint for orthopedics, which comprises a non-woven fabric support coated with a water-curable resin and, as outer layers of the support, a skin-protecting layer including polypropylene non-woven fabric and an outer surface layer in a network form, and to a method of manufacturing the same.

BACKGROUND ART

As conventional splints for orthopedics, plaster bandages or synthetic bandages have been used on the affected part of a patient suffering from a bone fracture, a muscular injury, or a sprain. In recent years, various fixation methods using synthetic splints have been employed.

Such a splint is structured in a manner such that various fibers are coated with a water-curable synthetic resin serving as a curing material, to thus constitute a support, which is then enveloped in a pad. Thus, the splint is applied at one time and is removably attached, and therefore is easy to use.

The materials used in the splint for orthopedics should have flexibility so that bendable portions are easily molded and should have sufficient mechanical strength to prevent a secondary injury.

The molding process requires a uniform setting time and an appropriate working time. After the application of the splint, a drying process should be efficiently realized in order to prevent a secondary injury attributable to the festering of the affected part.

In the case of the plaster bandage, it has been used as a splint for a long time, but is disadvantageous because it requires a long fitting time and setting time upon application thereof, is heavy, and has low strength relative to the weight thereof.

To make up for such problems, products in which glass fiber, polyester non-woven fabric, or polyester knitted fabric is coated with a water-curable resin to thus constitute a support have been developed.

However, in the case of the conventional splint using water-curable synthetic resin, the synthetic resin may flow out of the pad layer, undesirably compressing the skin of the patient, resulting in pains and injuries.

In addition, to solve the problems, products in which a pad is subjected to water-repellent treatment have been used, however these suffer because such treatment blocks the absorption of water and thus uniform curing is not realized, and furthermore, workability becomes poor, undesirably distorting the shape of the product applied to the affected part.

In addition, to make up for the problems, there have been proposed products in which a hydrophilic pad is used only for an outer surface layer thereof, and a water-repellent pad is used for a skin contact layer. However, water does not drain well due to the properties of the hydrophilic pad, and the drying time is lengthened, causing the patient to feel discomfort and the affected part to fester.

Also, since a hydrophilic agent is used to maintain hydrophilicity, the hydrophilicity of the product is decreased over time.

Consequently, to solve the problems, products in which double raschel is used to allow water to rapidly penetrate and drain have been developed. However, the use thereof is complicated because the skin-protecting layer is brought into direct contact with water and then dries. Thereby, the patient feels discomfort, and it is difficult to completely prevent the festering of the affected part.

Moreover, since the conventional products are all either dipped in water or sprayed with water to cure the water-curable resin, water inevitably enters the skin-protecting layer.

Therefore, the present invention is intended to completely prevent the entry of water into the skin-protecting layer.

DISCLOSURE OF INVENTION

Technical Problem

Accordingly, the present invention has been made keeping in mind the above problems encountered in the related art, and an object of the present invention is to provide a splint for orthopedics, which is structured such that water is supplied only to a support requiring water and is prevented from penetrating into a skin-protecting layer, thus completely eliminating the discomfort of a patient due to residual water and completely preventing the affected part from festering due to water, and to provide a method of manufacturing the same.

Technical Solution

In order to accomplish the above object, the present invention provides a splint for orthopedics, comprising a support, an aluminum casing directly provided on the support, and an outer surface layer and a skin-protecting layer, which are formed on the aluminum casing, unlike typical splints for orthopedics in which a surface layer and a skin contact layer are directly provided on a support. The support includes non-woven fabric coated with a water-curable resin, and is composed of 500~1500 g/m² of polyester non-woven fabric. The aluminum casing includes a combination of polyethylene, aluminum and nylon (or polyester), and the skin-protecting layer made of polypropylene non-woven fabric and the outer surface layer are provided thereon. The outer surface layer comprises material selected from among polyester, polypropylene, and nylon, and has a weight of 200~400 g/m².

In addition, in the splint of the present invention, the support comprises 500~1500 g/m² of needle-punched polyester non-woven fabric which is 60~60% impregnated with water-curable polyurethane. Further, the support is thinly coated with paraffin oil to avoid adhesion to the aluminum casing.

In addition, compared to conventional splints comprising a support, a skin-protecting layer and an outer surface layer provided on the support, and an aluminum casing provided on the skin-protecting layer and the outer surface layer, the splint of the present invention is characterized in that the aluminum casing is directly provided on the support, and the skin-protecting layer and the outer surface layer are provided on the aluminum casing.

In addition, in the splint of the present invention, the paraffin oil for use in separating the aluminum casing from the support includes liquid mineral oil, which is harmless to the human body.

BRIEF DESCRIPTION OF THE DRAWINGS

FIG. 1 is a perspective view showing the entire structure of the splint for orthopedics, according to the present invention;

FIG. 2 is an exploded perspective view showing the splint for orthopedics, according to the present invention; and FIGS. 3(a) to 3(c) are views showing the process of using the splint for orthopedics according to the present invention.

BEST MODE FOR CARRYING OUT THE INVENTION

Hereinafter, a detailed description will be given of the splint for orthopedics according to the present invention, with reference to the appended drawings.

FIG. 1 is a perspective view showing the entire structure of the splint for orthopedics according to the present invention, FIG. 2 is an exploded perspective view showing the splint for orthopedics according to the present invention, and FIGS. 3(a) to 3(c) are views showing the process of using the splint for orthopedics according to the present invention.

As shown in the drawings, in the splint for orthopedics of the present invention, an aluminum casing 2 separates a skin-protecting layer 3b and an outer surface layer 3a from a support 1. Hence, when the splint for orthopedics is applied, it enables the introduction of water only into the support 1, thus preventing the skin-protecting layer 3b and the outer surface layer 3a from coming into direct contact with water.

The support 1 is imparted with a supporting function by impregnating needle-punched polyester non-woven fabric with a water-curable resin. Further, in order to prevent difficulty in separating the aluminum casing 2 from the support 1 due to the stickiness of the water-curable resin, the support 1 includes paraffin oil. That is, the support 1 is thinly coated with paraffin oil, so that the aluminum casing 2 can be naturally separated therefrom, as shown in FIG. 3(c).

For use, as shown in FIG. 3(a), water is added into the aluminum casing 2 to react with water-curable urethane resin of the support 1, after which residual water is removed. As shown in FIG. 3(b), the aluminum casing 2 is removed, and then the splint seen in FIG. 3(c) is applied to the affected part of a patient.

The non-woven fabric used in the skin-protecting layer 3b, which is prepared through a needle punching process, functions to confer a soft feel to the patient when coming into contact with the skin of the patient and to protect the affected part of the patient from the support 1.

As such, if the non-woven fabric of the skin-protecting layer 3b has a low weight, pain may be caused on the affected part due to the compression of the support 1. On the other hand, if the non-woven fabric has a large weight, it is difficult to mold such fabric to be suitable for the affected part.

In the case of the support 1, a support coated with a water-curable resin is used. Preferably, a support 1 is used in a manner such that needle-punched polyester non-woven fabric having a weight of 500~1500 g/m² is 60~80% impregnated with a water-curable resin (NCO %=10~15%). Alternatively, as the support, 3~8 g/in·m of glass fiber woven fabric or polyester fiber woven fabric having 6~9 layers may be used.

When the fiber or non-woven fabric has a light weight, it is not strong enough to function as the support 1. On the other hand, when it is heavy, it is difficult to mold, and a resultant product is heavy and has poor ventilation.

The water-curable resin, which is applied on the support 1, includes a polyurethane prepolymer, and preferably has a viscosity ranging from 25,000 to 60,000 cps. When the viscosity exceeds the upper limit, the resin is not applied throughout the support 1, decreasing the strength of the support. On the other hand, when the viscosity is less than the lower limit, resin flow is increased, and the resin may flow out of the non-woven fabric. The water-curable resin preferably has an NCO % of 10~15% (weight ratio of isocyanate functional group). When the NCO % thereof exceeds the upper limit, a heating temperature is increased upon reaction between the resin and water, and thereby there exists the danger of secondary injury, and the viscosity of the resin may be decreased. On the other hand, when the NCO % is less than the lower limit, storage stability is decreased, and the viscosity is increased, and thus it is difficult to apply the resin on the support 1.

Furthermore, the support 1 is coated with paraffin oil 20~200 µm thick to separate the aluminum casing 2 in a pouch form therefrom. The paraffin oil includes liquid mineral oil, which is harmless to the human body.

In the case of the outer surface layer 3a, polyester non-woven fabric is used to prevent the danger of a secondary injury due to the support 1. Particularly useful is hydrophobic polyester non-woven fabric having a weight of 50~200 g/m². Since the splint of the present invention has no relationship with the penetration and drainage of water, it is possible to use any woven fabric and non-woven fabric that does not affect a mold.

In the case of the skin-protecting layer 3b, hydrophobic polypropylene non-woven fabric having a weight of 200~400 g/m² is used to avoid the contact between the water and the skin and to protect the skin from the support 1.

As mentioned above, the splint of the present invention is structured to bring the aluminum casing in a pouch form into direct contact with the support, therefore making it possible to solve conventional problems. Ultimately, problems related to the festering of the affected part and the discomfort of the patient can be completely solved. Furthermore, the setting time is uniform and the rapid application to the affected part is realized, thus increasing the convenience of a person who applies the splint.

Mode for the Invention

A better understanding of the present invention may be obtained in light of the following examples, which are set forth to illustrate, but are not to be construed as limiting the present invention.

Example 1

Dry non-woven fabric for a support 1 was prepared to have a weight of 500~1500 g/m² and a thickness of 2~5 mm, using a needle punching process, which was a mechanical bonding process.

As a water-curable resin to be applied on the support 1, a polyurethane prepolymer having NCO % (weight ratio) of 10~15% was used. The support was composed of the non-woven fabric, as a main component thereof, and the water-curable resin at a ratio of 7:3.

In order to separate an aluminum casing 2 from the support 1, the support coated with water-curable resin was further coated with liquid paraffin 20~200 mm thick. As such, liquid paraffin was selected from among liquid paraffin oils for cosmetics, available from Kukdong Oil & Chemicals Co. Ltd., Korea.

The aluminum casing 2 comprised a combination of nylon, aluminum and low-density polyethylene, and had a thickness of 110 µm.

Non-woven fabric for an outer surface layer 3a was prepared using hydrophobic polyester through a needle punching process. The outer surface layer composed of such non-woven fabric had a weight of 100 g/m².

For a skin-protecting layer 3b, a mechanical bonding type non-woven fabric was prepared using hydrophobic polypropylene through a needle punching process. The skin-protecting layer composed of such non-woven fabric had a weight of 320 g/m².

When the splint for orthopedics of the present invention was prepared, a support having a monolayer was compressed at a pressure of 5 kgf/cm², coated with a predetermined amount of a water-curable resin to have a ratio of the non-woven fabric to the water-curable resin of 7:3, and then further coated with liquid paraffin 100 μm thick. Thereafter, an aluminum casing, having two layers, was subjected to heat adhesion so that the support was enveloped therein, after which the outer surface layer and the skin-protecting layer were attached thereto using double-sided tape, thereby completing a product.

<Comparison of Products>

Depending on the types of product, hygroscopicity, drying time, and resin flowability were compared as follows. For comparison with the product of the invention, products A, B, C, and D, available from A, B, C, and D companies, respectively, were used.

As such, the outer surface layer was prepared using double raschel in network form (Polyester) in the product A of A company, hydrophobic polypropylene non-woven fabric in the product B of B company, water-repellent polyester spunlace non-woven fabric in the product C of C company, and hydrophilic polypropylene non-woven fabric in the product D of D company.

Test Example 1

To evaluate the hygroscopicity of the outer surface layer, 5 inch×45 inch sized samples were dipped in water for 10 sec, after which the setting time of the central portion thereof was measured according to ASTM F1536-95. In the case of the product of the present invention, which was structured to prevent the direct contact of water with the skin-protecting layer 3b and the outer surface layer 3a, the aluminum casing 2 was filled with water, and was then allowed to stand for 10 sec. In addition, to evaluate the thermal stability of the products, the products were stored in an oven at 70° C. for 30 days, and then subjected to the same comparison test.

Comparison of Inventive Product with General Products

TABLE 1

| material enveloping support | Inventive product aluminum casing | Product A double raschel in network form (Polyester) | Product B hydrophobic polypropylene non-woven fabric | Product C water-repellent polyester spunlace non-woven fabric | Product D hydrophilic polypropylene non-woven |
|---|---|---|---|---|---|
| Setting Time | 3 min 50 sec | 3 min 50 sec | 15 min | 20 min | 4 min |

Comparison of Products after 30 Days in Oven at 70° C.

TABLE 2

| material enveloping support | Inventive product aluminum casing | Product A double raschel in network form (Polyester) | Product B hydrophobic polypropylene non-woven fabric | Product C water-repellent polyester spunlace non-woven fabric | Product D hydrophilic polypropylene non-woven fabric |
|---|---|---|---|---|---|
| setting time | 3 min 50 sec | 3 min 50 sec | 15 min | 20 min | 15 min |

As is apparent from Table 1, the products using the hydrophilic non-woven fabric of D company and the double raschel of A company, and the product of the invention had excellent water penetrability. As is apparent from Table 2, the product using the hydrophilic polypropylene non-woven fabric of D company aged due to heat, and undesirably exhibited water repellency again.

Consequently, the product of the invention was advantageous because water was brought into direct contact not with the skin-protecting layer 3b or the outer surface layer 3a but with the support 1 to react with the support, and thus the inventive product did not affect the aging or the setting time.

Test Example 2

In order to detect the time required to dry the wet product, the following drying test was conducted. The results are shown in Table 3 below.

(Test of Drying Product)

1. Initial weight of a 5 inch×45 inch sized product was measured.

2. In order to introduce a sufficient amount of water into the product, the material enveloping the support was opened wide and then the product was all either dipped in water for 10 sec. In the case of the product of the invention, the aluminum casing was filled with water and then allowed to stand for 10 sec.

3. The product was taken out of the water, and the wet product was dried using dry towel, and then the weight of the product was measured. In the case of the product of the invention, the aluminum casing and the water were simultaneously removed.

4. The product was folded in two and then dried in an oven at 70° C.

5. The weight of the product was measured over time, and the residual water content of the product was calculated as a percentage.

$$\text{initial water content \%} = \frac{\text{weight of product in water} - \text{initial product weight}}{\text{initial product weight}} \times 100$$

-continued $$\text{residual water content \%} = \frac{\text{weight of product in water} - \text{dried product weight}}{\text{weight of product in water} - \text{initial product weight}} \times 100$$

Results of Test of Drying Products

TABLE 3

| | | Inventive product aluminum casing | Product A double raschel in network form (Polyester) | Product B hydrophobic polypropylene non-woven fabric | Product C water-repellent polyester spunlace non-woven fabric | Product D hydrophilic polypropylene non-woven fabric |
|---|---|---|---|---|---|---|
| material enveloping support | initial water content | 1.5% | 11.9% | 25.3% | 27.4% | 20.5% |
| drying time/ residuial water content over time | 5 min | 70% | 43% | 19% | 12% | 31% |
| | 10 min | 100% | 70% | 31% | 22% | 49% |
| | 15 min | | 86% | 41% | 29% | 57% |
| | 20 min | | 95% | 50% | 37% | 70% |
| | 25 min | | 100% | 57% | 45% | 78% |
| | 30 min | | | 65% | 52% | 85% |
| | 35 min | | | 70% | 57% | 90% |
| | 40 min | | | 75% | 61% | 95% |
| | 45 min | | | 79% | 65% | 98% |
| | 50 min | | | 82% | 70% | 100% |
| | 55 min | | | 85% | 73% | |
| | 60 min | | | 89% | 77% | |
| | 80 min | | | 99% | 88% | |
| | 100 min | | | 100% | 95% | |
| | 120 min | | | | 100% | |

As is apparent from Table 3, in the case of the product of the invention, the water was added into the aluminum casing and then was removed together with the aluminum casing. Thereby, all of the residual water, other than the water required for the reaction, was much more rapidly removed, compared to the other products.

The product of the invention had low initial water content, and thus the drying time thereof was decreased, so that no water remained. Unlike conventional products having water added throughout them, in the product of the invention, water was supplied only to the support requiring water. Accordingly, a patient did not feel discomfort due to water, thereby preventing the affected part from festering.

Industrial Applicability

As described hereinbefore, the present invention provides a splint for orthopedics and a method of manufacturing the same. According to the present invention, in the splint for orthopedics using a water-curable resin, it is easy to introduce water. Further, no water is supplied to the portion of the splint that comes into contact with the skin of a patient, thus decreasing the time required to dry the splint. Thereby, the splint of the invention is advantageous in that the affected part of the patient can be prevented from festering, and the discomfort of the patient can be completely eliminated.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A splint for orthopedics for supporting an affected part of a patient suffering from a fracture or a sprain, comprising
a support for supporting the affected part,
a skin-protecting layer and an outer surface layer, which are outer layers of the support, and
an aluminum casing provided between the support and the skin-protecting layer and between the support and the outer surface layer, so that water is introduced only into the support and is not brought into direct contact with the skin-protecting layer and the outer surface layer upon application of the splint for orthopedics,
wherein the support comprises a non-woven fabric having a weight of 500~1500 g/m$^2$, the non-woven fabric being 60-80% impregnated with a water-curable resin, and
wherein the support is coated with paraffin oil.

2. A method of preparing a splint for orthopedics for supporting an affected part of a patient suffering from a fracture or a sprain, comprising:
a first step of providing a support comprising polyester non-woven fabric having a weight of 500~1500 g/m$^2$, an aluminum casing comprising a combination of nylon, aluminum and low-density polyethylene, an outer surface layer comprising hydrophobic polyester non-woven fabric having a weight of 50~200 g/m$^2$, and a skin-protecting layer comprising hydrophobic polypropylene non-woven fabric having a weight of 200~400 g/m$^2$;
a second step of coating the support with a water-curable resin comprising a polyurethane prepolymer having an NCO % of 10~15% so that the non-woven fabric for the support is 60~80% impregnated with the water-curable resin;
a third step of further coating the support, coated with the water-curable resin, with paraffin oil, in order to easily separate the aluminum casing from the support;
a fourth step of subjecting the aluminum casing, which has two layers, to heat adhesion, so that the support subjected to the third step is enveloped therein; and
a fifth step of disposing the outer surface layer and the skin-protecting layer on both outer surfaces of the aluminum casing enveloping the support, and then attaching them thereto.

* * * * *